(12) United States Patent
Kuehling (10) Patent No.: US 8,790,392 B2
(45) Date of Patent: *Jul. 29, 2014

(54) ENDOPROSTHESIS COATING

(75) Inventor: Michael Kuehling, Munich (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 252 days.

This patent is subject to a terminal disclaimer.

(21) Appl. No.: 13/115,618

(22) Filed: May 25, 2011

(65) Prior Publication Data

US 2011/0224783 A1 Sep. 15, 2011

Related U.S. Application Data

(63) Continuation of application No. 11/776,320, filed on Jul. 11, 2007, now Pat. No. 8,002,823.

(51) Int. Cl.
*A61F 2/82* (2013.01)
*A61F 2/06* (2013.01)

(52) U.S. Cl.
USPC .................................................. 623/1.46

(58) Field of Classification Search
USPC .............................................. 623/1.15–1.48
See application file for complete search history.

(56) References Cited

U.S. PATENT DOCUMENTS

| | | |
|---|---|---|
| 5,091,205 A | 2/1992 | Fan |
| 5,951,881 A | 9/1999 | Rogers et al. |
| 5,980,566 A | 11/1999 | Alt et al. |
| 6,290,721 B1 | 9/2001 | Heath |
| 6,776,094 B1 | 8/2004 | Whitesides et al. |
| 6,971,813 B2 | 12/2005 | Shekalim et al. |
| 2002/0144757 A1 | 10/2002 | Craig et al. |
| 2003/0018380 A1 | 1/2003 | Craig et al. |
| 2003/0077200 A1 | 4/2003 | Craig et al. |
| 2004/0143317 A1 | 7/2004 | Stinson et al. |
| 2004/0236399 A1 | 11/2004 | Sundar |
| 2005/0019265 A1 | 1/2005 | Hammer et al. |
| 2005/0070990 A1 | 3/2005 | Stinson |
| 2005/0208100 A1* | 9/2005 | Weber et al. ............. 424/426 |
| 2005/0216074 A1 | 9/2005 | Sahatjian et al. |
| 2006/0038027 A1 | 2/2006 | O'Connor et al. |
| 2006/0153729 A1 | 7/2006 | Stinson et al. |
| 2006/0194008 A1 | 8/2006 | Schwartz et al. |
| 2008/0071350 A1* | 3/2008 | Stinson ..................... 623/1.15 |
| 2008/0071355 A1* | 3/2008 | Weber et al. ............. 623/1.16 |
| 2008/0071358 A1* | 3/2008 | Weber et al. ............. 623/1.42 |
| 2008/0262412 A1* | 10/2008 | Atanasoska et al. ......... 604/20 |
| 2008/0294236 A1 | 11/2008 | Anand et al. |
| 2008/0294246 A1 | 11/2008 | Scheuermann et al. |
| 2009/0018647 A1 | 1/2009 | Benco et al. |

OTHER PUBLICATIONS

Duwez et al., "Mechanochemistry: targeted delivery of single molecules," Nature Nanotechnology, vol. 1, pp. 122-125, (2006).

(Continued)

*Primary Examiner* — Suzette J Gherbi
(74) *Attorney, Agent, or Firm* — Fish & Richardson P.C.

(57) ABSTRACT

An endoprosthesis, such as a stent, includes anchoring regions formed of polymer that enhance adherence of a coating, e.g. a drug eluting polymer coating, to a stent surface, e.g. made of ceramic. The anchoring regions can be formed using stamping processes.

18 Claims, 11 Drawing Sheets

(56) References Cited

OTHER PUBLICATIONS

International Preliminary Report on Patentability issued on Jan. 21, 2010 by the WIPO in PCT application No. PCT/US2008/069579, filed Jul. 10, 2008.

International Search Report and Written Opinion issued on Dec. 1, 2009 by the European Patent Office in PCT application No. PCT/US2008/069579, filed Jul. 10, 2008.

Schetsky, "Shape Memory Alloys", Encyclopedia of Chemical Technology (3rd ed.), John Wiley & Sons, vol. 20, pp. 726-736, (1982).

\* cited by examiner

EHT = 1.00 kV  Signal A = InLens  Chamber = 1.25e-003 Pa
Mag = 75.00 KX    WD = 3 mm

FIG. 4A 100 nm

EHT = 1.00 kV  Signal A = InLens  Chamber = 1.39e-003 Pa
Mag = 75.00 KX    WD = 3 mm

ENDOPROSTHESIS COATING

CROSS-REFERENCE TO RELATED APPLICATIONS

This application is a continuation of and claims the benefit of priority under 35 U.S.C. 120 to U.S. Application Ser. No. 11/776,320, filed Jul. 11, 2007, the entire contents of which are hereby fully incorporated by reference.

TECHNICAL FIELD

The invention relates to endoprosthesis coating.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, examples of which include stents, stent-grafts, and covered stents.

Many endoprostheses can be delivered inside the body by a catheter. Typically the catheter supports a reduced-size or compacted form of the endoprosthesis as it is transported to a desired site in the body, for example the site of weakening or occlusion in a body lumen. Upon reaching the desired site the endoprosthesis is installed so that it can contact the walls of the lumen.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn. Stent delivery is further discussed in Heath, U.S. Pat. No. 6,290,721.

SUMMARY

In an aspect, the invention features an endoprosthesis with a body including a ceramic on a surface thereof, a pattern of spaced polymeric anchoring elements adhered to the ceramic, and a polymeric coating adhered to the anchoring elements.

In another aspect, the invention features a method of forming an endoprosthesis including providing an endoprosthesis having a ceramic on a surface, applying to the surface an anchoring polymer, patterning the anchoring polymer to form anchors, and applying a polymer coating to the anchors.

Embodiments may include one or more of the following. The polymeric coating includes a drug. The ceramic is an oxide or nitride. The ceramic is IROX. The thickness of the anchoring elements is less than the thickness of the coating. The thickness of the anchoring elements is about 10-90% of the thickness of the coating. The width of the anchoring elements is less than the height of the anchoring elements. The thickness of the anchoring elements is about 1 to 10 micron. The anchoring elements form a covalent bond to the ceramic. The anchoring elements are formed of silane. The anchoring elements include hydrophobic moieties.

Embodiments may also include one or more of the following. The polymeric coating is adhered to the anchoring elements without covalent bonding. The ceramic has a globular morphology. The ceramic has a defined grain morphology. The anchoring elements extend into the ceramic. The anchoring elements are substantially free of drug. The anchoring polymer is patterned by stamping to form regions of different thickness. The anchoring polymer is patterned after stamping.

Embodiments may include one or more of the following advantages. An endoprosthesis, such as a stent, can be provided with a polymer coating, such as a drug eluting coating, that is strongly adhered to the stent to reduce flaking or delamination. The stent can include a ceramic material, and the polymer coating can be a material that has desirable drug release characteristics but non-optimal adhesion characteristics to the ceramic material. The adhesion can be enhanced without substantially increasing the thickness of the polymer coating, or modifying its drug delivery or biocompatibility characteristics. The stent can include a patterned first polymer directly on a ceramic surface, e.g. IROX, that has good bonding characteristics to the ceramic. The pattern can be an intermittent series of separated lands that act as anchors. The first, anchor polymer also has good bonding characteristics to a second polymer. The second polymer is coated over the first polymer and any exposed ceramic. The second polymer, e.g. a drug eluting polymer, is adhered strongly to the first polymer. The pattern and first polymer anchors expose a large surface for adherence to the second polymer and provides a form fit for the second polymer.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figures 1A, 1B, 1C:
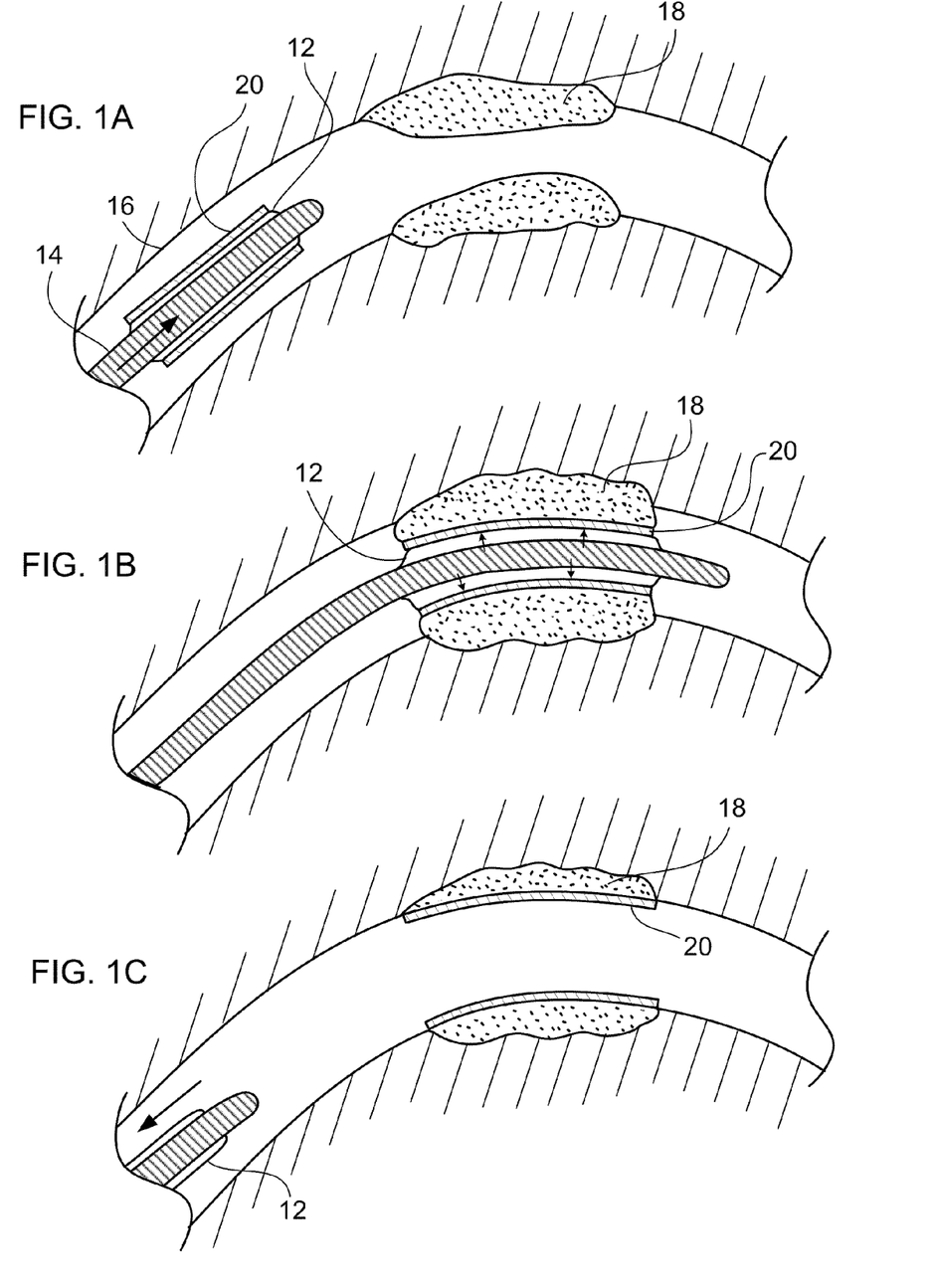
FIGS. 1A-1C are longitudinal cross-sectional views illustrating delivery of a stent in a collapsed state, expansion of the stent, and deployment of the stent.

Referring to FIGS. 1A-1C, a stent 20 is placed over a balloon 12 carried near a distal end of a catheter 14, and is directed through the lumen 16 (FIG. 1A) until the portion carry the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2A:
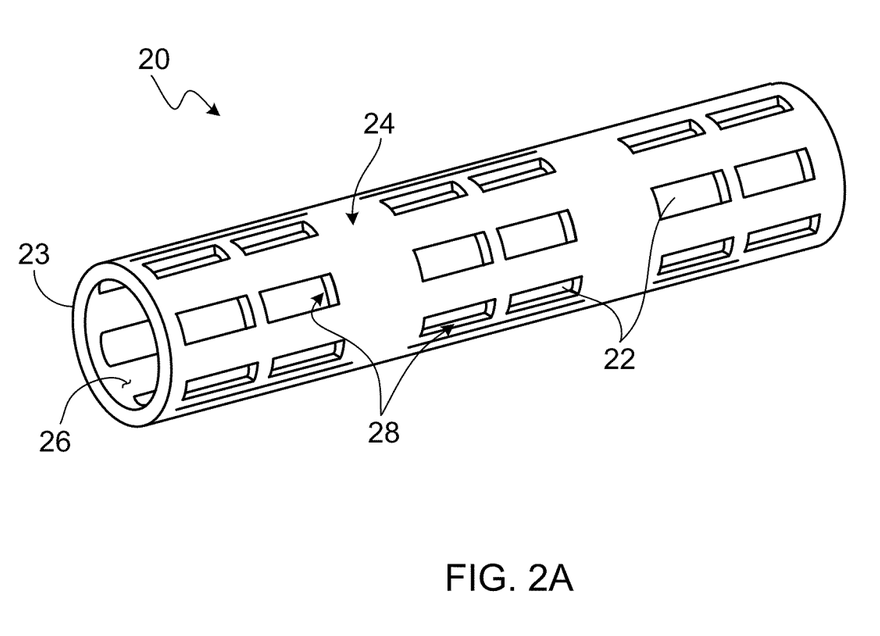
FIG. 2A is a perspective view of a stent.

Referring to FIG. 2A, the stent 20 includes a plurality of fenestrations 22 defined in a wall 23. Stent 22 includes several surface regions, including an outer, or abluminal, surface 24, an inner, or luminal, surface 26, and a plurality of cutface surfaces 28. The regions of the wall defining the fenestrations are sometimes referred to as stent struts. The stent can be balloon expandable, as illustrated above, or self-expanding stent. In embodiments, the stent includes a body made of e.g. a metal such as stainless steel, chrome, nickel, cobalt, tantalum, niobium (columbium), superelastic alloys such as nitiniol, cobalt chromium, MP35N, and other metals. Suitable stent materials and stent designs are described in Heath '721, supra.

Figure 2B:
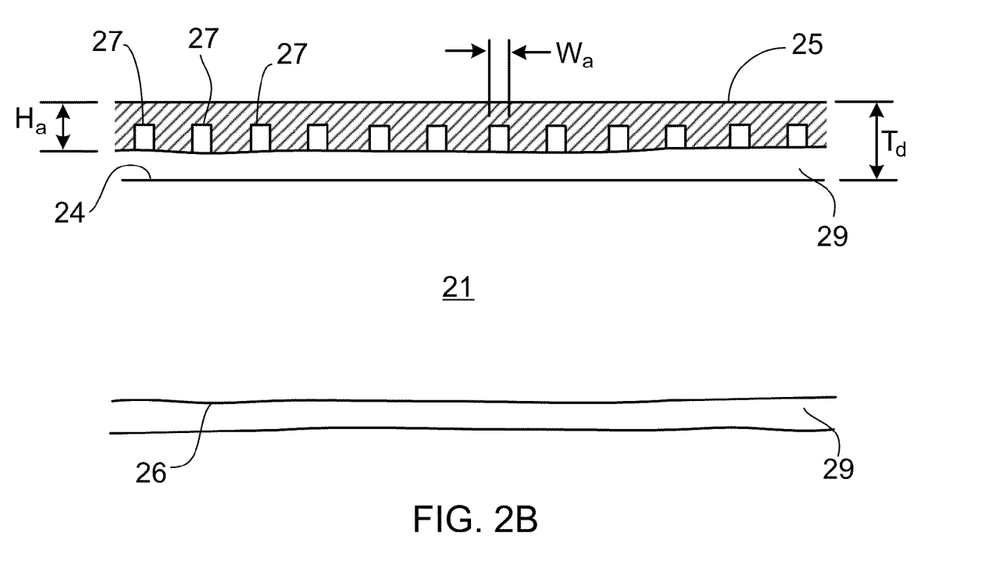
FIG. 2B is a cross sectional view of a portion of a stent wall.

Referring to FIG. 2B, a cross-section through a stent wall illustrating abluminal and luminal regions, the stent 20 includes a body 21, e.g. a metal. On the abluminal and adluminal surfaces 24, 26 of the body, the stent includes a layer 29 of a material effective to enhance stent function, such as a ceramic, e.g. Iridium dioxide (IROX), that enhances stent endothelialization. The abluminal surface 24 further includes a coating 25 of a polymer that enhances function by, e.g. eluting a drug. The adherence of the coating 25 to the stent is enhanced by a pattern of anchoring elements 27 which are bound tightly to the ceramic layer 29. The anchoring elements 27 are formed of a polymer with good adhesion properties to both the ceramic and the polymer in the coating 25. The pattern increases the surface area for bonding between the coating 25 and the anchoring elements 27.

In embodiments, the anchoring elements 27 are formed of polymers such as silanes which can form Si—O bonds with a ceramic surface or have non-covalently bonded adhesive interactions with the surface. The silanes can be modified for compatibility with the drug eluting polymer coating 25. For example, the silanes can be modified with moieties that adjust hydrophobicity/hydrophilicity for compatibility with the polymer coating 25 or moieties that cross-link with the polymer coating 25.

In embodiments, the anchoring polymer can be a tie layer with hydrophyllic groups that adheres strongly to, e.g. a ceramic oxide, and hydrophobic groups that adhere to hydrophobic polymers suitable for drug release. Suitable polymers for anchoring elements 27 include the same polymer as the drug eluting polymer coating. In embodiments, the anchoring elements 27 are formed of a different polymer than the drug eluting polymer coating. In embodiments, the anchoring elements are substantially free of drug, thus reducing the residual drug that remains on the stent. The anchoring elements can be covalently or non-covalently bonded to the ceramic.

In embodiments, the anchoring elements 27 have a height, $H_a$, of about 10-80% of the thickness, $T_d$, of the drug eluting polymer coating 25. The elements 27 have a width, $W_a$, of about 10 to 200% of their height, $H_a$. In embodiments, the height, $H_a$, is about 1-10 micron. Formation of silane layer is discussed further in Duwez, *Nature Nanotechnology*, 1, 122-125 (2006). A suitable drug eluting polymer is SIBS. Other suitable materials for layers 23, 25 and anchoring elements are discussed below. Suitable polymers are described in U.S. patent application Ser. No. 11/776,304, filed contemporaneously herewith.

Figure 3A:
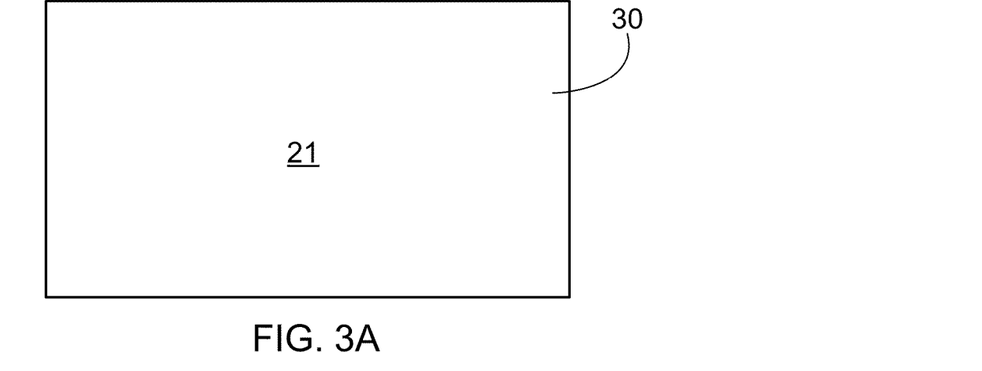
FIGS. 3A-3I are cross-sectional views illustrating a method for forming a stent.
Figure 3B:
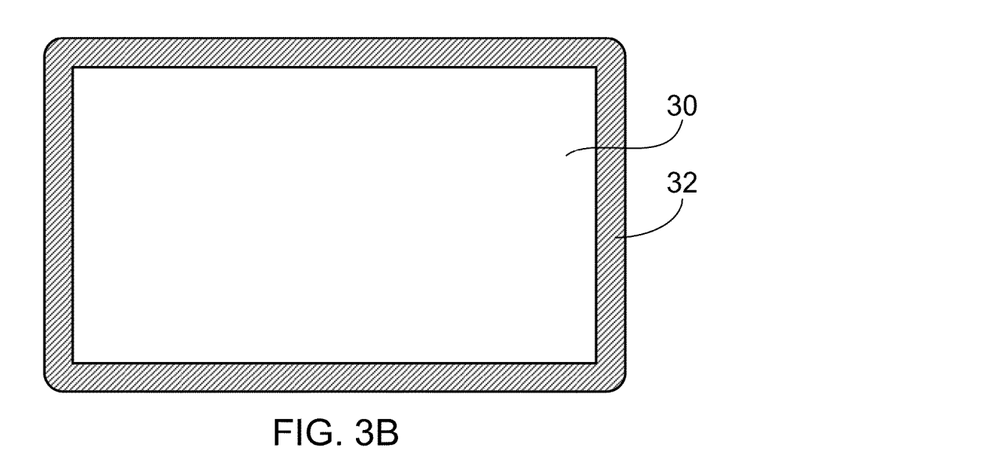
Figure 3C:
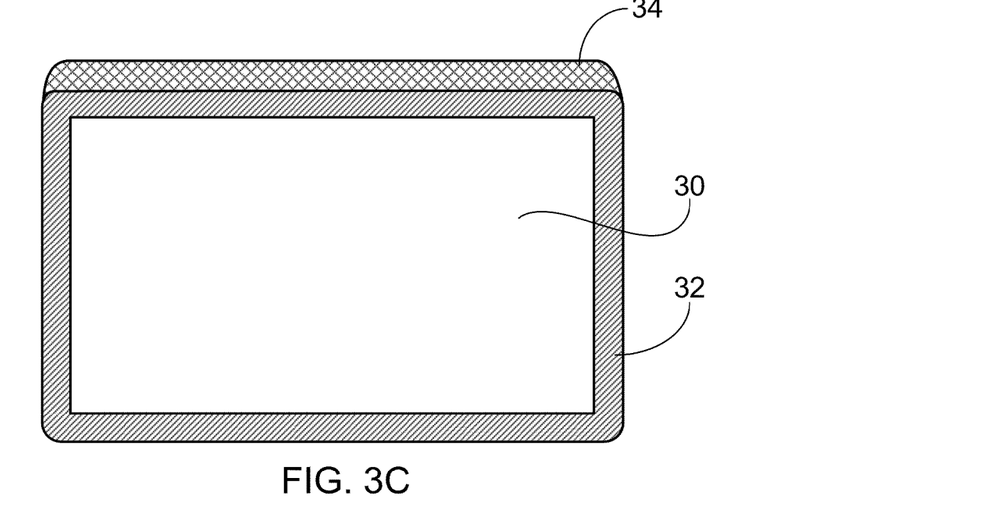

Referring to FIGS. 3A-3I, cross-sectional views of stent strut, a technique for forming a stent is illustrated. Referring particularly to FIGS. 3A and 3B, the stent strut 30 includes a body 21 onto which is formed a coating 32 of ceramic, such as IROX. Referring to FIG. 3C, a polymeric coating is 34 is deposited over the coating 32 on a selected side of the strut, such as the abluminal side. The coating 34 may be a polymer or a polymer precursor. Polymeric coating 34 is coated by, e.g. rolling, dipping or spraying.

Figure 3D:
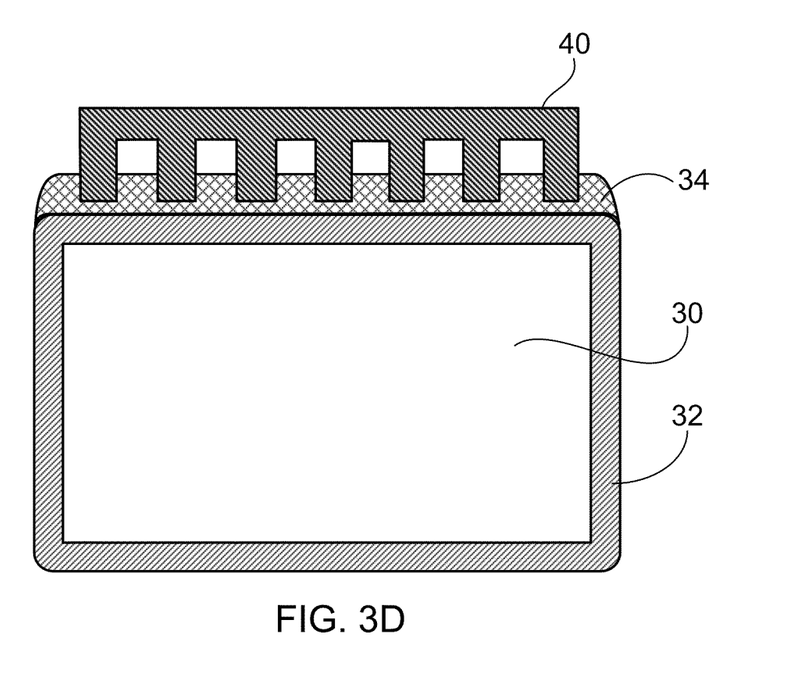
Figure 3E:
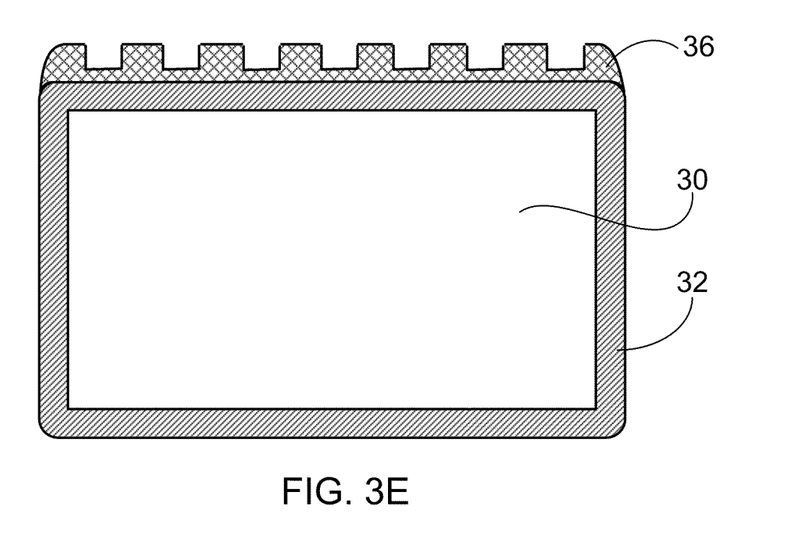

Referring to FIG. 3D, the coating 34 is imprinted with a pattern by a stamp 40. The stamp 40 has protrusions 42 which are brought into contact with polymer coating, 34, e.g. while the polymer is still wet and malleable. Referring specifically to FIG. 3E, stamp 40 is removed from the polymer coating 34 to reveal patterned polymer (or polymer precursor) 36 containing surface relief features corresponding to the inverse of those of stamp 40. The patterned polymer is then dried or cured. Stamp 40 can be made of metal, ceramic, plastic, a relatively hard polymer, or the like. For example, the stamp 40 can formed of a silicone elastomer, such as a polydimethylsiloxane. Protrusions 42 may take a variety of desirable shapes, e.g. rectangular, circular, curved, etc., and may have straight or curved sidewalls. Protrusions 40 may also be formed of either continuous or discontinuous regions. The protrusions can be formed by etching, laser ablation or molding. Techniques for forming patterns with small features are discussed in Rogers, U.S. Pat. Nos. 5,951,881 and 6,776,094. Contact patterning is discussed in U.S. Pat. No. 6,971,813.

Figure 3F:
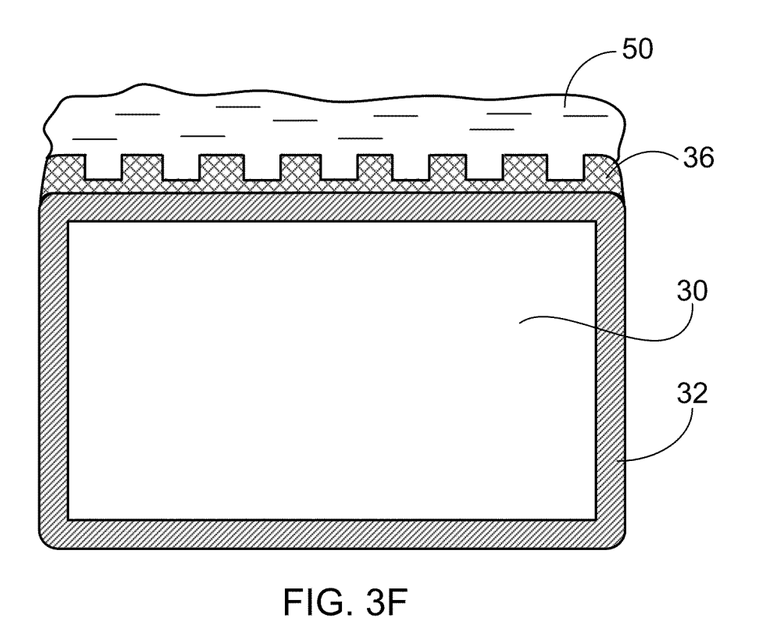

Referring to FIG. 3F, the patterned polymer (or polymer precursor) 36 is etched, reducing the thickness of the polymer 36 and revealing portions of the underlying coating 32. In embodiments, patterned polymer 36 is etched by a wet-chemical etchant 50. Suitable wet-chemical etchants may include phosphoric, acetic, and nitric acids and water in a specific ratio. In an alternative embodiment, polymer 36 may be removed by plasma etching, e.g. with oxygen or ozon. With another alternative technique polymer 36 may be removed by use of laser ablation, for example by ultrashort lasers or UV-excimer lasers. Other applicable processes for polymer 36 removal may be ion bombardment or ion implantation. In other embodiments, the patterned polymer is used without etching, etc. in which case regions of the ceramic are not exposed but rather a thin layer of anchoring polymer remains between adjacent anchoring elements.

Figure 3G:
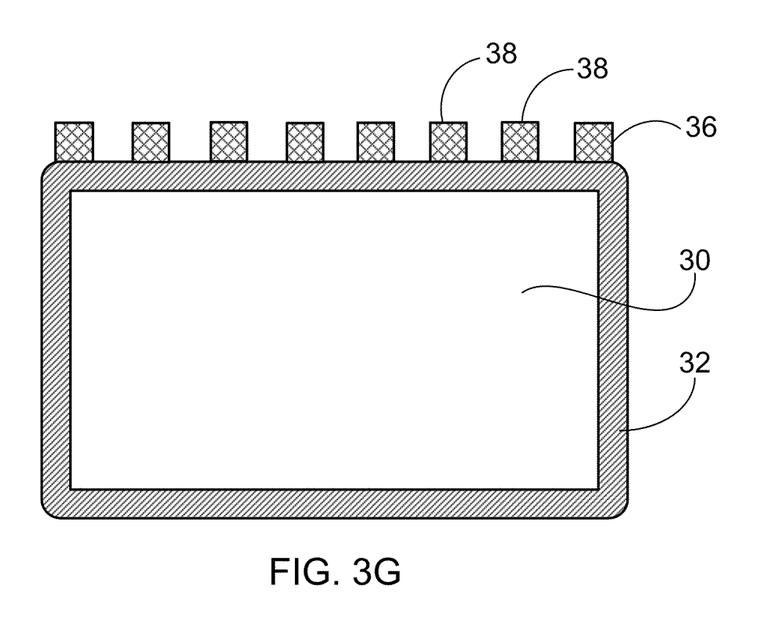
Figure 3H:
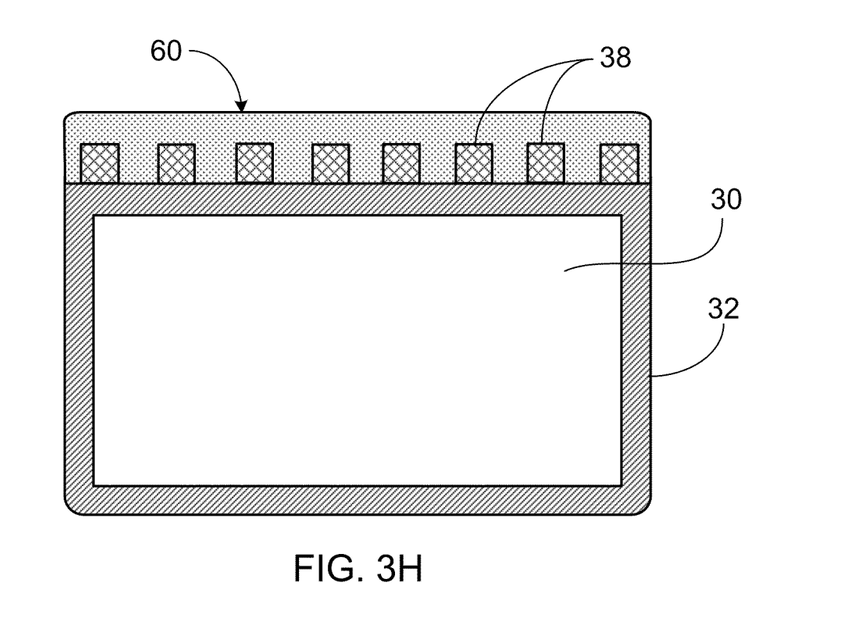

Referring particularly to FIG. 3G, the etching process forms a pattern of anchoring elements 38, bonded to the coating 32. Referring to FIG. 3H, a second polymer (or polymer precursor) 60 is coated over and form-fits around the anchoring elements. The polymer 60 can be dried, polymerized, and/or cross-linked to the anchoring elements.

Figure 3I:
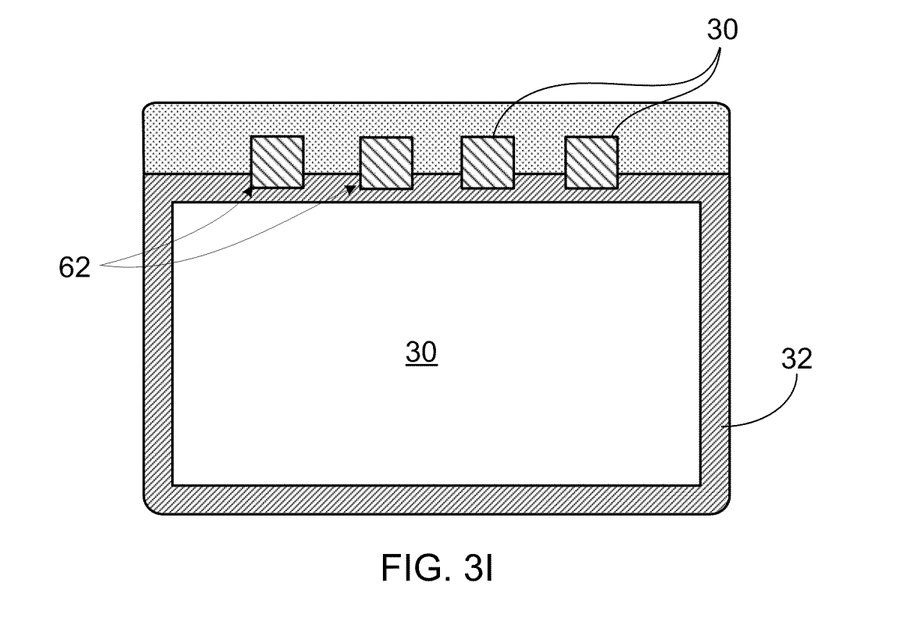

Referring to FIG. 3I, in an alternative embodiment, the anchoring elements extend into wells 62 defined by the ceramic. The wells can be formed by, e.g. laser ablation etching after deposition of the ceramic (FIG. 3B).

The morphology and composition of the ceramic is selected for its mechanical characteristics, to enhance adhesion to the stent body and enhance adhesion of a polymer coating, for example, and/or to enhance therapeutic function such as reducing restenosis and enhancing endothelialization. Certain ceramics, e.g. oxides, can reduce restenosis through the catalytic reduction of hydrogen peroxide and other precursors to smooth muscle cell proliferation. The oxides can also encourage endothelial growth to enhance endothelialization of the stent. When a stent is introduced into a biological environment (e.g., in vivo), one of the initial responses of the human body to the implantation of a stent, particularly into the blood vessels, is the activation of leukocytes, white blood cells which are one of the constituent elements of the circulating blood system. This activation causes a release of reactive oxygen compound production. One of the species released in this process is hydrogen peroxide, $H_2O_2$, which is released by neutrophil granulocytes, which constitute one of the many types of leukocytes. The presence of $H_2O_2$ may increase proliferation of smooth muscle cells and compromise endothelial cell function, stimulating the expression of surface binding proteins which enhance the attachment of more inflammatory cells. A ceramic such as iridium oxide (IROX) can catalytically reduce $H_2O_2$. The morphology of the ceramic can enhance the catalytic effect and reduce growth of endothelial cells. Iridium oxide (IROX) is discussed further in Alt, U.S. Pat. No. 5,980,566. Defined grain morphologies may also allow for greater freedom of motion and are less likely to fracture as the stent is flexed in use and thus the coating resists delamination of the ceramic from an underlying surface and reduces delamination of an overlaying polymer coating. The stresses caused by flexure of the stent, during expansion or contraction of the stent or as the stent is delivered through a tortuously curved body lumen increase as a function of the distance from the stent axis. As a result, in embodiments, a morphology with defined grains is particularly desirable on abluminal regions of the stent or at other high stress points, such as the regions adjacent fenestrations which undergo greater flexure during expansion or contraction.

Figure 4A:
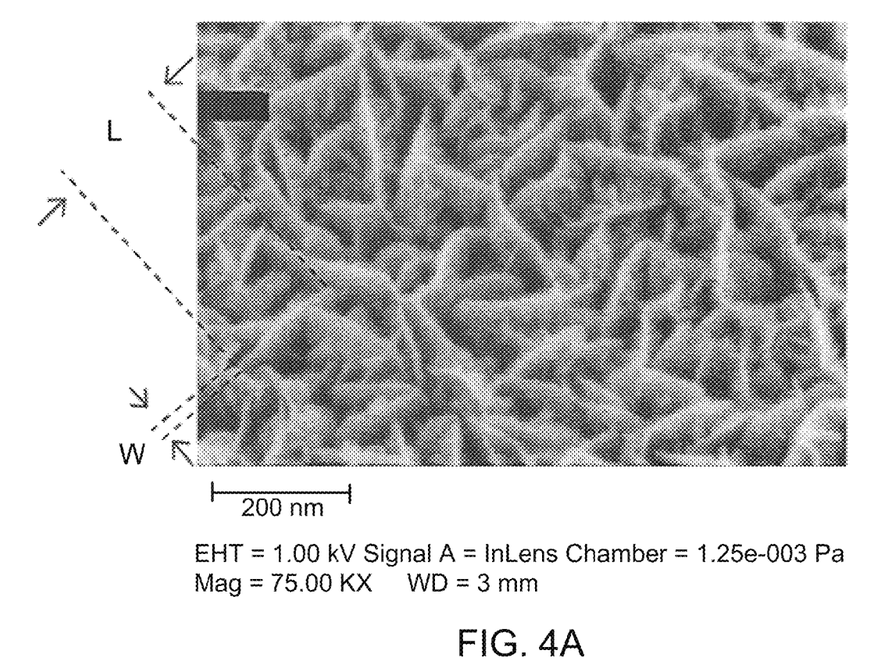
FIGS. 4A and 4B are plan views of morphologies.

The morphology of the surface of the ceramic is characterized by its visual appearance, its roughness, and/or the size and arrangement of particular morphological features such as local maxima. In embodiments, the surface is characterized by definable sub-micron sized grains. Referring particularly to FIG. 4A, for example, in embodiments, the grains have a length, L, of the of about 50 to 500 nm, e.g. about 100-300 nm, and a width, W, of about 5 nm to 50 nm, e.g. about 10-15 nm. The grains have an aspect ratio (length to width) of about 5:1 or more, e.g. 10:1 to 20:1. The grains overlap in one or more layers. The separation between grains can be about 1-50 nm. In particular embodiments, the grains resemble rice grains.

Figure 4B:
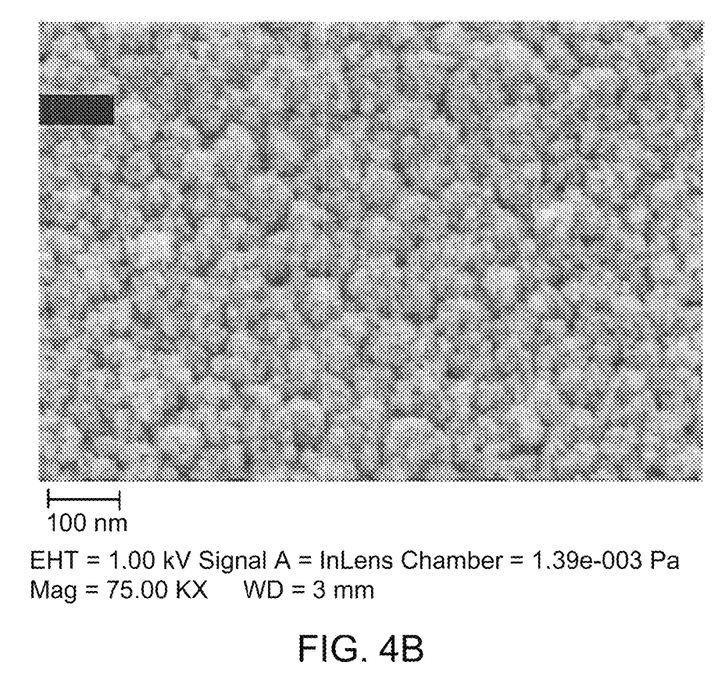

Referring particularly to FIG. 4B, in embodiments, the surface is characterized by a more continuous surface having a series of globular features separated by striations. The striations have a width of about 10 nm or less, e.g. 1 nm or less, e.g. 1 nm or about 0.1 nm. The striations can be generally randomly oriented and intersecting. The depth of the striations is about 10% or less of the thickness of the coating, e.g. about 0.1 to 5%. In embodiments, the surface resembles an orange peel. In other embodiments, the surface has characteristics between high aspect ratio definable grains and the more continuous globular surface. For example, the surface can include low aspect ratio lobes or thin planar flakes. The morphology type is visible in FESEM images at 50 KX.

The roughness of the surface is characterized by the average roughness, Sa, the root mean square roughness, Sq, and/or the developed interfacial area ratio, Sdr. The Sa and Sq parameters represent an overall measure of the texture of the surface. Sa and Sq are relatively insensitive in differentiating peaks, valleys and the spacing of the various texture features. Surfaces with different visual morphologies can have similar Sa and Sq values. For a surface type, the Sa and Sq parameters indicate significant deviations in the texture characteristics. Sdr is expressed as the percentage of additional surface area contributed by the texture as compared to an ideal plane the size of the measurement region. Sdr further differentiates surfaces of similar amplitudes and average roughness. Typically Sdr will increase with the spatial intricacy of the texture whether or not Sa changes.

In embodiments, the ceramic has a defined grain type morphology. The Sdr is about 30 or more, e.g. about 40 to 60. In addition or in the alternative, the morphology has an Sq of about 15 or more, e.g. about 20 to 30. In embodiments, the Sdr is about 100 or more and the Sq is about 15 or more. In other embodiments, the ceramic has a globular type surface morphology. The Sdr is about 20 or less, e.g. about 8 to 15. The Sq is about 15 or less, e.g. about less than 8 to 14. In still other embodiments, the ceramic has a morphology between the defined grain and the globular surface, and Sdr and Sq values between the ranges above, e.g. an Sdr of about 1 to 200 and/or an Sq of about 1 to 30.

Figure 5A:
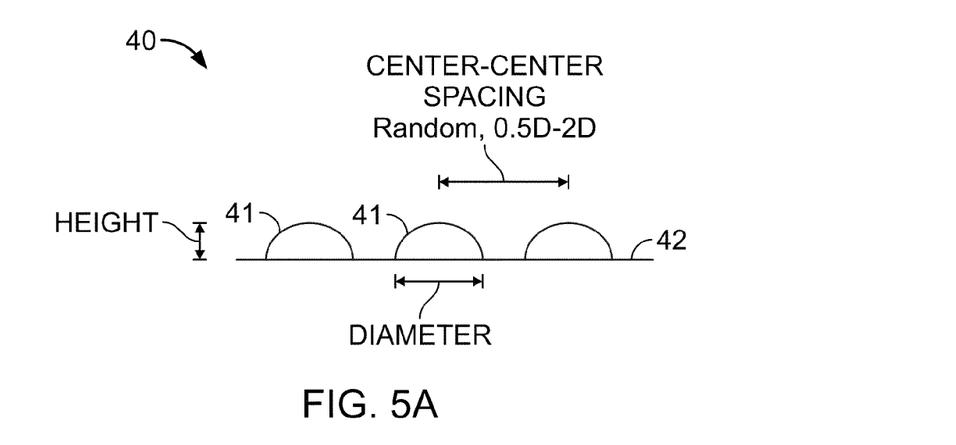
FIGS. 5A-5C are schematics of morphologies.
Figure 5B:
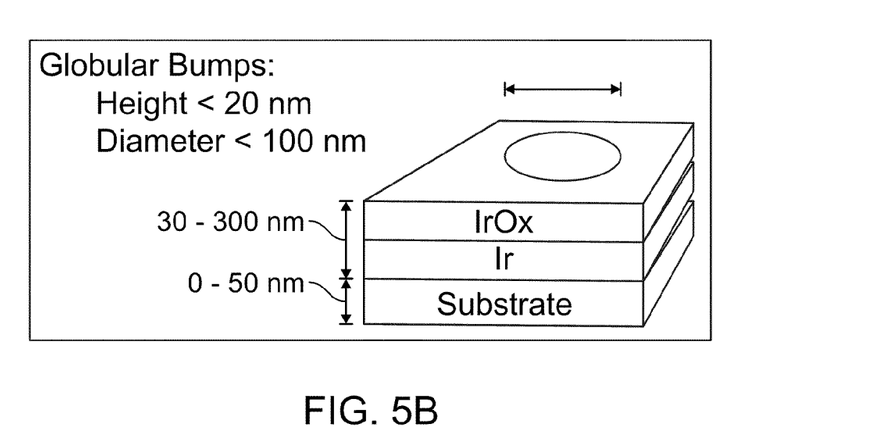
Figure 5C:
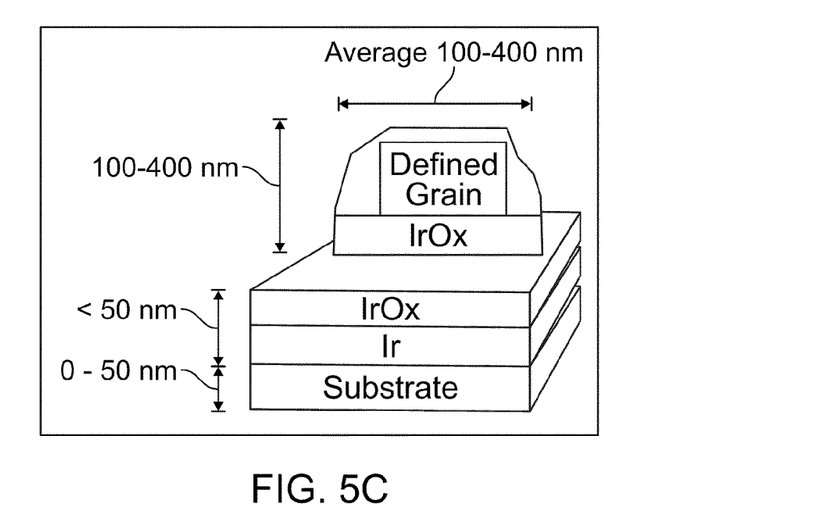

Referring to FIGS. 5A-5C, morphologies are also characterized by the size and arrangement of morphological features such as the spacing, height and width of local morphological maxima. Referring particularly to FIG. 5A, a coating 40 on a substrate 42 is characterized by the center-to-center distance and/or height, and/or diameter and/or density of local maxima. In particular embodiments, the average height, distance and diameter are in the range of about 400 nm or less, e.g. about 20-200 nm. In particular, the average center-to-center distance is about 0.5 to 2× the diameter.

Referring to FIG. 5B, in particular embodiments, the morphology type is a globular morphology, the width of local maxima is in the range of about 100 nm or less and the peak height is about 20 nm or less. In particular embodiments, the ceramic has a peak height of less than about 5 nm, e.g., about 1-5 nm, and/or a peak distance less than about 15 nm, e.g., about 10-15 nm. Referring to FIG. 5C, in embodiments, the morphology is defined as a grain type morphology. The width of local maxima is about 400 nm or less, e.g. about 100-400 nm, and the height of local maxima is about 400 nm or less, e.g. about 100-400 nm. As illustrated in FIGS. 5B and 5C, the select morphologies of the ceramic can be formed on a thin layer of substantially uniform, generally amorphous IROX, which is in turn formed on a layer of iridium metal, which is in turn deposited on a metal substrate, such as titanium or stainless steel. The spacing, height and width parameters can be calculated from AFM data.

Further discussion of morphologies and a suitable computational technique is provided in U.S. patent application Ser. Nos. 11/752,772 and 11/752,736, filed May 23, 2007. Suitable ceramics include metal oxides and nitrides, such as of iridium, zirconium, titanium, hafnium, niobium, tantalum, ruthenium, platinum and aluminum. The ceramic can be crystalline, partly crystalline or amorphous. The ceramic can be formed entirely of inorganic materials or a blend of inorganic and organic material (e.g. a polymer). In other embodiments, the morphologies described herein can be formed of metal. In embodiments, the thickness T of the coatings is in the range of about 50 nm to about 2 um, e.g. 100 nm to 500 nm.

Figure 6:
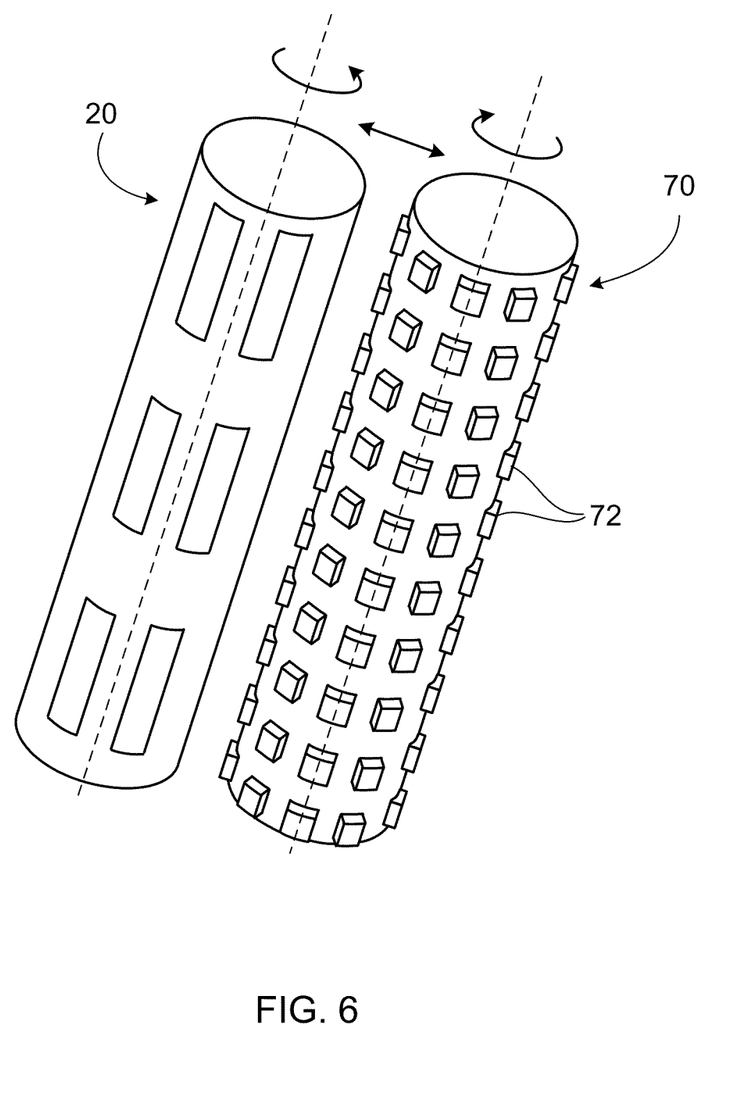
FIG. 6 is a perspective view of a stent positioned to rotationally contact a stamp.
Figure 7:
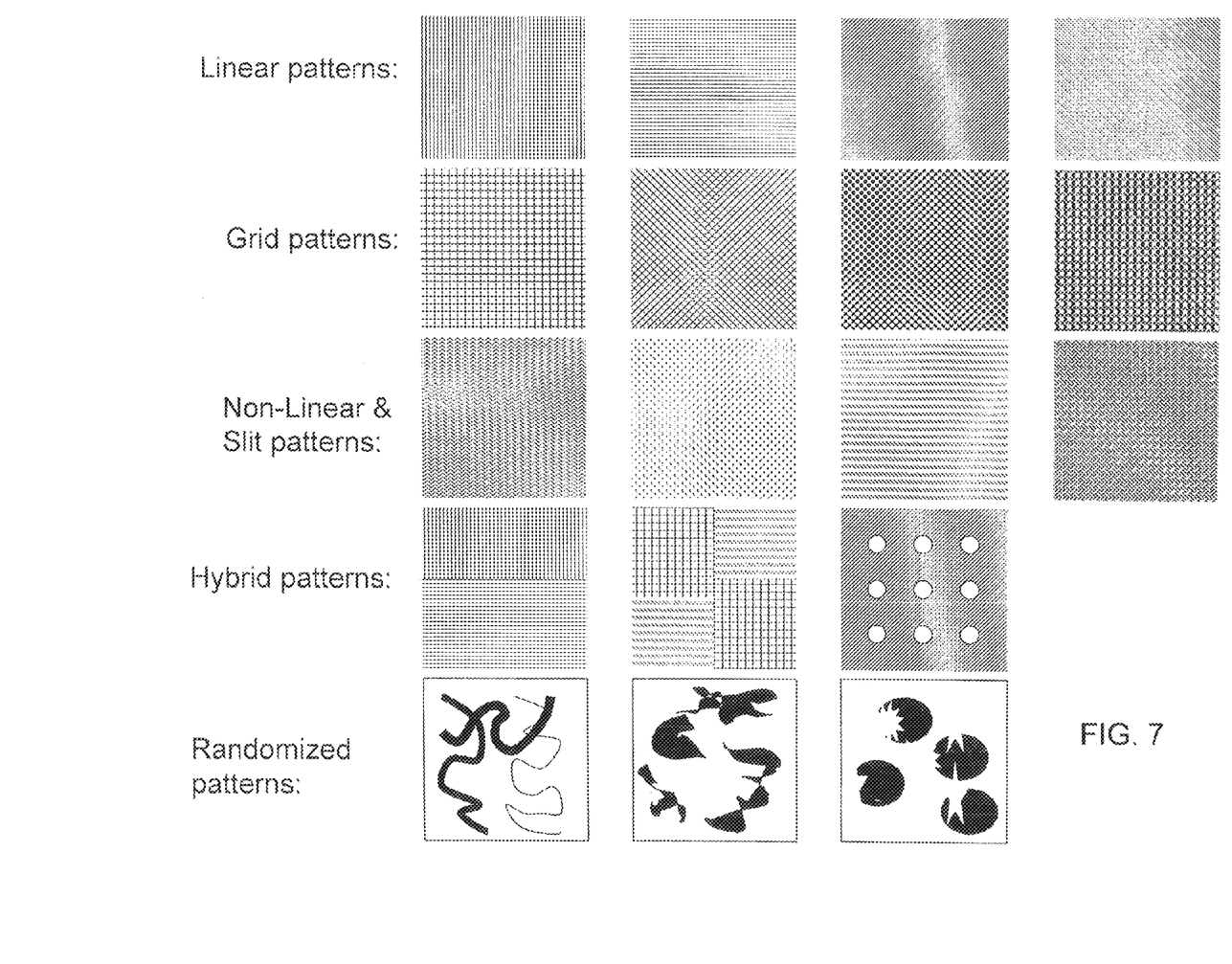
FIG. 7 is a plan view illustrating anchoring patterns.

Referring to FIG. 6, a system for imprinting a pattern includes a rotatable cylinder 70 with a pattern of protrusions 72. The cylinder 70 is placed into proximity with a stent 20 mounted for rotation such that, upon rotation (arrows) of the cylinder 70 and the stent 20, the protrusions imprint a pattern on the stent. Referring to FIG. 7, exemplary patterns are illustrated. Nonlinear patterns, e.g. sinsordial wave patterns can be implemented. The pattern can also be a non-repeating random series of protrusions of various shapes and at various positions.

Suitable polymers for the anchoring elements and/or the drug eluting polymers are described in U.S. patent application Ser. No. 11/776,304, filed contemporaneously herewith. Similar polymers may be hydrophilic or hydrophobic, and may be selected, without limitation, from polymers including, for example, polycarboxylic acids, cellulosic polymers, including cellulose acetate and cellulose nitrate, gelatin, polyvinylpyrrolidone, cross-linkedpolyvinylpyrrolidone, polyanhydrides including maleic anhydride polymers, polyamides, polyvinyl alcohols, copolymers of vinyl monomers such as EVA, polyvinyl ethers, polyvinyl aromatics such as polystyrene and copolymers thereof with other vinyl monomers such as isobutylene, isoprene and butadiene, for example, styrene-isobutylene-styrene (SIBS) copolymers, styrene-isoprene-styrene (SIS) copolymers, styrene-butadiene-styrene (SBS) copolymers, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenerated polyalkylenes including polytetrafluoroethylene, natural and synthetic rubbers including polyisoprene, polybutadiene, polyisobutylene and copolymers thereof with other vinyl monomers such as styrene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL.®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment, the preferred polymer is polyacrylic acid, available as HYDROPLUS.® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyiocyanates such that the devices become instantly lubricious when exposed to body fluids. In another preferred embodiment of the invention, the polymer is a copolymer of polylactic acid and polycaprolactone. Suitable polymers are discussed in U.S. Publication No. 20060038027.

The polymer is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Published Patent Application No. 2005/0216074. Polymers for drug elution coatings are also disclosed in U.S. Published Patent Application No. 2005/019265A.

Suitable materials for layer 23 include coatings that enhance biocompatibility, reduce proliferation, and facilitate endothelialization. Materials include ceramics, such as ceramic oxides and nitrides of iridium, titanium, and zirconium. The ceramics can be formed by sputtering or wet chemical techniques. A particular oxide is IROX which is further discussed in U.S. Pat. No. 5,980,566 and U.S. Ser. No. 10/651,562 filed Aug. 29, 2003. The layer 23 can be, e.g. 10-1000 nm in thickness.

In embodiments, the anchoring elements and layer 23 are provided only on the abluminal surface, as illustrated. In other embodiments, these elements are provided as well or only on the abluminal surface and/or cut-face surfaces.

The stents described herein can be configured for vascular, e.g. coronary and peripheral vasculature or non-vascular lumens. For example, they can be configured for use in the esophagus or the prostate. Other lumens include biliary lumens, hepatic lumens, pancreatic lumens, uretheral lumens and ureteral lumens.

Any stent described herein can be dyed or rendered radio-opaque by addition of, e.g., radio-opaque materials such as barium sulfate, platinum or gold, or by coating with a radio-opaque material. In embodiments, the porous structure can be formed directly on the stent body, as described above, or the porous structure can be formed in a coating over the stent body. The coating may be, e.g., a radio-opaque metal. The stent can include (e.g., be manufactured from) metallic materials, such as stainless steel (e.g., 316L, BioDur® 108 (UNS S29108), and 304L stainless steel, and an alloy including stainless steel and 5-60% by weight of one or more radio-paque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a super-elastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., U.S. Pat. No. 6,290,721).

All publications, patent applications, patents, and other references mentioned herein are incorporated by reference herein in their entirety.

Still further embodiments are in the following claims.

What is claimed is:

1. An endoprosthesis, comprising:
a body including a ceramic on a substrate,
a pattern of spaced polymeric anchoring elements adhered to the ceramic, at least some of the spaced polymeric anchoring elements projecting outward from a surface of the ceramic, and
a polymeric coating adhered to the anchoring elements,
wherein the ceramic is free of a polymer forming the anchoring elements.

2. The endoprosthesis of claim 1, wherein the polymeric coating includes a drug.

3. The endoprosthesis of claim 1, wherein the anchoring elements extend into wells defined in the ceramic.

4. The endoprosthesis of claim 1, wherein the ceramic comprises an oxide or a nitride.

5. The endoprosthesis of claim 4, wherein the ceramic comprises iridium dioxide.

6. The endoprosthesis of claim 1, wherein a width of each anchoring element is less than a height of the anchoring element.

7. The endoprosthesis of claim 1, wherein the thickness of the anchoring elements is about 1 to 10 micron.

8. The endoprosthesis of claim 1, wherein the anchoring elements form a covalent bond to the ceramic, and optionally wherein the anchoring elements include hydrophobic moieties.

9. An endoprosthesis, comprising:
a body including a ceramic on a substrate,
a pattern of spaced polymeric anchoring elements adhered to the ceramic, at least some of the spaced polymeric anchoring elements extending beyond a surface of the ceramic, and
a polymeric coating adhered to the anchoring elements,
wherein the ceramic is free of a polymer forming the anchoring elements, wherein the anchoring elements are formed of silane.

10. The endoprosthesis of claim 1, wherein the polymeric coating is adhered to the anchoring elements without covalent bonding.

11. The endoprosthesis of claim 1, wherein the ceramic has a globular morphology, or a defined grain morphology.

12. The endoprosthesis of claim 1, wherein the anchoring elements extend into the ceramic.

13. The endoprosthesis of claim 1, wherein the anchoring elements are free of any drug.

14. A method of forming an endoprosthesis, comprising:
providing an endoprosthesis including a ceramic on a substrate;
applying to the ceramic an anchoring polymer;
patterning the anchoring polymer to form anchors, at least some of the anchors extending beyond a surface of the ceramic, wherein patterning the anchoring polymer comprises stamping the anchoring polymer to form regions of different thickness; and
applying a polymer coating to the anchors,
wherein the ceramic is free of the anchoring polymer.

15. The method of claim 14, wherein patterning the anchoring polymer further comprises etching the anchoring polymer after stamping.

16. The method of claim 14, wherein the anchors are free of any drug.

17. The method of claim 14, wherein the ceramic comprises IROX.

18. The method of claim 14, wherein the polymer coating includes a drug.

* * * * *